United States Patent [19]

Bayer et al.

[11] Patent Number: 4,690,132

[45] Date of Patent: Sep. 1, 1987

[54] ENDOSCOPE PARTICULARLY USEFUL AS AN ANOSCOPE

[76] Inventors: Izhak Bayer, 58 Ahad Ha'am Street, Herzlia; Amnon Adoram, 14 Kaplanski Street, Givatayim, both of Israel

[21] Appl. No.: 849,212

[22] Filed: Apr. 7, 1986

[30] Foreign Application Priority Data

Apr. 9, 1985 [IL] Israel .......................... 74847

[51] Int. Cl.⁴ .......................... A61B 1/00; A61B 17/02
[52] U.S. Cl. ............................................ 128/4; 128/20
[58] Field of Search .......................... 128/20, 3, 4, 5, 6, 128/7

[56] References Cited

U.S. PATENT DOCUMENTS 2,012,597  8/1935  Cameron .................................. 128/6
3,132,645  5/1964  Gasper .................................... 128/3

FOREIGN PATENT DOCUMENTS 2708071  8/1978  Fed. Rep. of Germany .......... 128/3

Primary Examiner—William H. Grieb
Attorney, Agent, or Firm—Benjamin J. Barish

[57] ABSTRACT

An endoscope device particularly useful as an anoscope, includes three sections each of the configuration of a segment of a cylinder. Two of the sections are pivotable to each other to a tubular position wherein the three sections define a tubular endoscope insertable into a body cavity for examination, or to an open position wherein the two pivotable sections define a retractor for retracting tissue in the body cavity to facilitate performing a clinical treatment therein. The device further includes a mandrel receivable within the sections of the endoscope when in their tubular positions to facilitate the insertion of the endoscope into the body cavity.

18 Claims, 4 Drawing Figures

ENDOSCOPE PARTICULARLY USEFUL AS AN ANOSCOPE

BACKGROUND OF THE INVENTION

The present invention relates to endoscopes, namely to instruments insertable into a body cavity for examination purposes. The invention is particularly applicable to anoscopes insertable into the anus for examining various body conditions in the rectum, and is therefore described below with respect to this application.

The conventional anoscope is in the form of a metal tube of hollow cylindrical configuration which, together with a mandrel received within it, is insertable into the anus. After the anoscope has thus been inserted, the mandrel is removed, thereby enabling the physician to examine the interior of the rectum. Sometimes, anoscope includes an illuminating means, such as a fiber optic bundle, for illuminating the interior of the rectum to facilitate its examination.

It frequently happens that as a result of the examination, it is necessary to perform some clinical treatment within the rectum. When this is required, the anoscope is removed, and a retractor is usually inserted to retract tissues in order to perform the required clinical treatment. This procedure is time-consuming and inconvenient to the examining physician, and is particularly unpleasant and sometimes painful to the patient.

SUMMARY OF THE INVENTION

An object of the present invention is to provide an endoscope, particularly useful as an anoscope, having advantages in the above respects, in that it is capable of not only serving the normal function of an endoscope or anoscope to permit examination of the interior of the body cavity, but also the normal function of a retractor to allow clinical treatment within the body cavity.

According to a broad aspect of the present invention, there is provided an endoscope device particularly useful as an anoscope, characterized in that it includes a plurality of sections each of the configuration of a segment of a cylinder, at least two of the sections being pivotable to each other to a tubular position wherein the plurality of sections define a tubular endoscope insertable into a body cavity for examining same, or to an open position wherein the pivotable section define a retractor for retracting tissue in the body cavity to facilitate performing a clinical treatment therein.

More particularly, the endoscope device comprises three sections, namely, a first section, a second section pivotable to the first section along one edge thereof, and a third section attachable to the first and second section along their opposite edges to define therewith the tubular endoscope in the tubular position of the sections, but detachable from the first and second sections to permit them to be pivoted to their tubular positions to define the retractor.

The third section is slidably attached to the first and second sections and is formed at its opposite edges with ribs received in recesses in the first and second sections.

According to further features included in the described preferred embodiment, the pivotable sections are each attached to a handle to facilitate holding the endoscope and pivoting its sections either to their tubular or open positions. One of the handles carries a toothed rack received within a slot formed in the other handle for releasably retaining the two handles in the tubular or open position of the plurality of sections.

It will be seen that an endoscope constructed in accordance with the foregoing features provides a number of advantages which are particularly important when the endoscope is used as an anoscope. Thus, the device, in its tubular configuration, may be inserted into the body cavity and used as an endoscope or anoscope in the normal manner for examining the interior of the body cavity. If a clinical treatment is required, the removable section may be slid off the two pivotable sections, and the two pivotable sections may then be opened by moving the handles to the desired position, for using the device as a retractor in order to retract tissues in the body cavity for purposes of the clinical treatment. The novel device may thus perform the combined functions of the usual endoscope (or anoscope) and retractor, thereby saving the physician considerable time and inconvenience, and the patient considerable pain and unpleasantness, which would otherwise be involved in removing the endoscope (or anoscope) from the body cavity and then inserting a retractor in order to perform the required clinical treatment.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
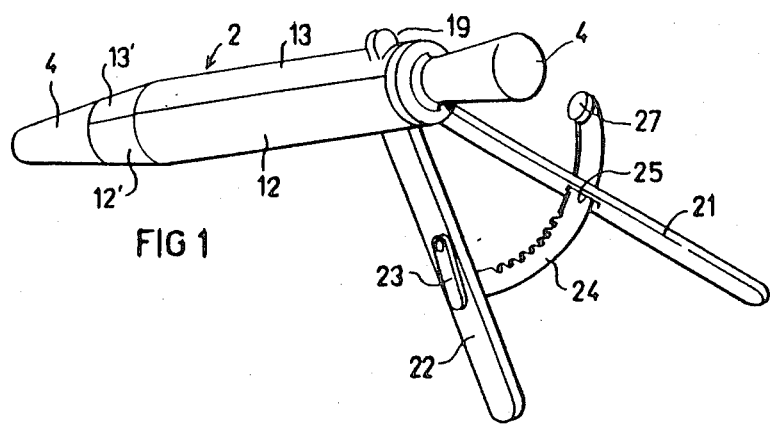
FIG. 1 is a three-dimensional view illustrating one form of endoscope, particularly an anoscope, constructed in accordance with the present invention.

The device illustrated in the drawings is partiularly useful as an anoscope for insertion into the anus of a person in order to examine the condition of the rectum. The anoscope includes a cylindrical tube 2 and a mandrel 4 received within tube 2 and inserted therewith into the anus. The purpose of mandrel 4 is merely to facilitate the insertion of tube 2; once the latter has been inserted, the mandrel is removed, thereby permitting visual examination of the interior of the rectum via tube 2.

Figure 2:
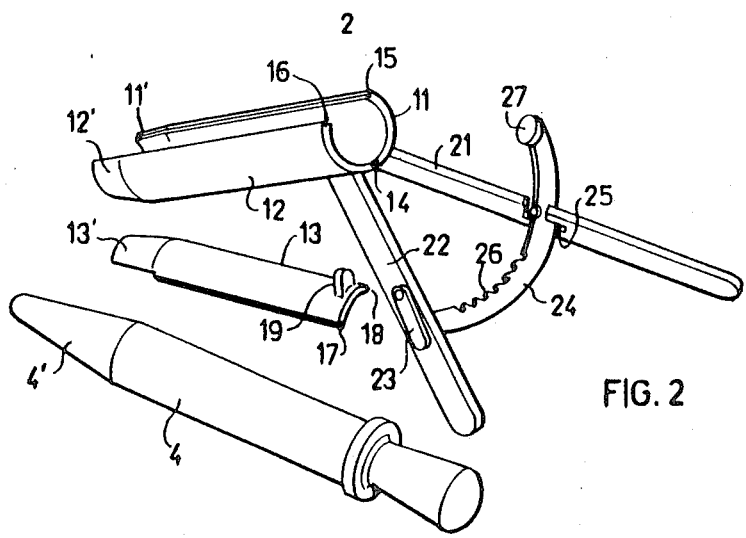
FIG. 2 is an exploded view illustrating the parts of the anoscope of FIG. 1 in their disassembled condition.

In accordance with the present invention, tube 2 is constituted of a plurality of section 11, 12 and 13, best seen in FIG. 2. Sections 11 and 12 are pivotably mounted to each other a long one edge, shown at 14 in FIG. 2; and section 13 is slidably attachable to sections 11 and 12 to complete the cylindrical configuration. For this purpose, the opposite edges of sections 11 and 12 are formed with grooves 15, 16 extending for the complete length of the sections; and the opposite edges of the removable section 13 are reduced in thickness to define ribs 17, 18, received within grooves 15 and 16. Removable section 13 is further formed with a finger-gripping projection 19 to facilitate attaching and detaching that section from the two pivotable sections 11 and 12.

Each of the three sections 11, 12, 13, defines a segment of a cylinder such that when the three sections are attached together and disposed in the configuration illustrated in FIG. 1, they define a complete cylinder as in a conventional anoscope. The leading end of each of the three sections 11, 12 and 13 is tapered, as shown at 11', 12', 13' in FIGS. 1 and 2; and the thicknesses of these tapered sections are also tapered. This construction thus provides a gradually tapered leading end for the cylindrical tube flush with the correspondingly tapered leading end 4' of mandrel 4 to facilitate insertion of the tube with the mandrel into the body cavity.

The two pivotable sections 11 and 12 of the anoscope tube are provided with handles 21, 22 secured to the rear ends of the two sections. Handle 22 carries a leaf spring 23 on which is mounted one end of a curved toothed rack 24 passing through handle 22 and extending in the direction of handle 21. Handle 21 is formed with a slot 25 through which the toothed rack 24 passes. A mid-portion of rack 24 is formed with a plurality of teeth 26 along the upper edge of the rack. The end tip carries a finger piece 27 engageable by the user's finger to pivot rack 24 within slot 25, and thereby to release the rack from engagement with the upper edge of slot 25 in order to move handle 21 toward or away from handle 22.

Figure 3:
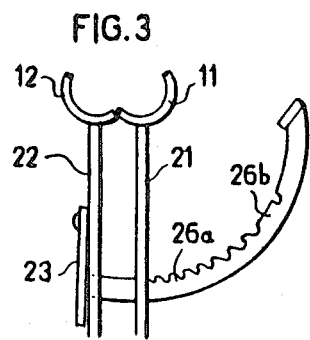
FIG. 3 and 4 illustrate two positions of the device of FIG. 1 in its retractor configuration
Figure 4:
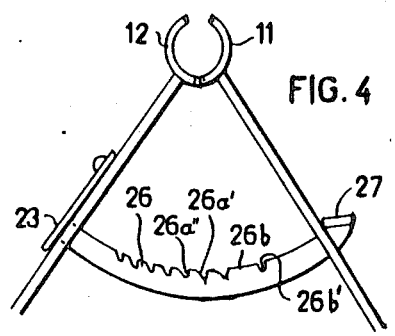

Teeth 26 formed on the upper edge of rack 24 are of a special configuration, best seen in FIGS. 3 and 4.

Thus, as shown in these figures, most of the teeth, therein designated 26a, are formed with a slanted face 26a,' on one side of the tooth permitting handle 21 to be moved towards handle 22 merely by the application of a squeezing pressure, since the slanted faces causes the rack 24 to pivot by its mounting on spring 23 when handle 21 is moved in this direction. However, the opposite faces 26a" of these teeth are perpendicular to the rack axis so that movement of the handle in the opposite direction, i.e. to spread apart the two handles, requires the user to press down on fingerpiece 27 order to pivot rack 24 to disengage the rack from the edge of slot 25 in handle 21.

Rack 24, includes a further tooth 26b which has right-angel faces 26b', 26b"at both its sides. Face 26b' at the outer side of the tooth determines the position of handle 21 with respect to handle 22, and thereby the position of the two pivotable sections 11, 12, to define the positions of these two pivotable section for receiving the slidable section 13 in order to produce the tubular configuration of the device as illustrated in FIG. 1. Thus, when handles 21 are 22 are in their fully open condition as illustrated in FIG. 4, the user only needs to squeeze handle 21 towards handle 22; handle 21 will thus move towards handle 22 until its slot 25 engages face 26b' of rack 26, whereupon the two pivotable sections 11, 12 will be located in proper positions to receive the removable section 13 for using the instrument as an endoscope or anoscope for examination purposes. Any other position of the two pivotable sections 11 and 12 requires the user to press down finger piece 27 of rack 24 in order to release handle 21 for movement towards or away from handle 22.

FIG. 1 illustrates the normal condition of the instrument when used as an endoscope or anoscope. In this normal condition, handle 21 is pivoted to the position with respect to handle 22 such that the upper edge of slot 25 in handle 21 sits within recess 26b'of rack 26 carried by handle 22. In this position of the two pivotable sections 11, 12, the removable section 13 may be attached to the two pivotable sections 11, 12 by sliding the edge ribs 17, 18 of section 13 into the end grooves 15, 16 of the pivotable sections 11, 12. Mandrel 4 may be inserted within the tube 2 either before or after the latter has been configured to the tubular configuration including all three sections 11, 12 and 13.

With mandrel 4 received within the tube 2, the latter may be inserted into the body cavity, and then the mandrel may be removed to permit visual examination of the interior of the body cavity. The examination may be performed under normal lighting conditions, or may be facilitated by the inclusion of a fiber optic bundle (not shown), e.g., clipped to the underside of the pivotable sections 11, 12, to illuminate the area to be examined.

If some clinical treatment is required as a result of the examination, section 13 of the endoscope tube 2 may be removed by gripping its finger piece 19 and withdrawing it from grooves 15, 16 of the two pivotable sections 11, 12. The two pivotable sections 11, 12 may then serve as a retractor for retracting tissue in the body cavity as may be required for performing the clinical treatment. Thus, handles 21, 22 may be pivoted towards each other, as shown in FIG. 3, in order to open sections 11, 12. The handles may be moved apart in order to close the two sections, as shown in FIG. 4; or they may be moved to any intermediate position, as desired according to the particular situation.

Handle 21 may be freely moved by a squeezing pressure alone towards handle 22 to open the pivotable sections 11, 12 as shown in FIG. 3 because of the slanted faces 26a' of the teeth formed in rack 24. However, to move them to the closed position of the two pivotable sections 11, 12 requires the user to depress finger piece 27 because of perpedicular faces 26a" of teeth 26a. Moreover, tooth 26b, because of its straight face 26b', fixes the position of handle 21 with respect to handle 2 such that the two pivotable sections 11 and 12 are in proper positions to receive the slidable section 13 in order to form the tubular configuration of the endoscopic tube 2; therefore, this position of the handles, when moved from their outermost positions (FIG. 4), is effected automatically by a mere squeezing pressure. To move the two handles away from this position requires the depression of finger piece 27.

While the invention has been described with respect to a preferred emodiment, it will be appreciated that many modifications may be made. For example, the device could include more than two pivotable sections. Further, an illuminating device may be include, such as a fiber optic bundle, e.g., clipped to the underside of the tube 2. Many other variations, modifications and applications of the invention may be made.

What is claimed is:

1. An endoscope device particularly useful an an anoscope, characterized in that it includes a plurality of sections each of the configuration of a segment of a cylinder, said plurality of sections comprising a first section, a second section pivotable to said first section along one edge thereof, and a third section attachable to said first and second sections along their opposite edges to define therewith a tubular endoscope insertable into a body cavity for examining same, said thrid section being detachable from said first and second sections permitting said first and second sections to be pivoted to an open position wherein they define a retractor for retracting tissue in the body cavity to facilitate performing a clinical treatment therein.

2. The device according to claim 1, wherein the outer surfaces of said plurality of sections are each tapered at one end so that they together define, when in their tubular positions, a cylinder whose outer surface is conically shaped at its leading end.

3. The device according to claim 1, further including a mandrel receivable within said plurality of sections of the endoscope when in their tubular positions to facilitate the insertion of the endoscope into the body cavity.

4. The device according to claim 1, wherein said thrid section is slidably attachable to said first and second sections, said third section being formed at each of its opposite edges with a rib slidably received in a groove formed in the edge of each of said first and second sections.

5. The device according to claim 1, wherein said pivotable sections are each attached to a handle to facilitate holding the device and pivoting said sections to their tubular or open portions.

6. The device according to claim 5, wherein one of said handles carries a toothed rack received within a slot formed in the other handle for releasably retaining the two handles in the tubular or open positions of the plurality of sections.

7. The device according to claim 6, wherein said toothed rack pivotably mounted to said one handle is spring-biassed into engagement with the edge of the slot in the second handle to releasably retain the two handles in their positions.

8. The device according to claim 7, wherein said toothed rack is curved and is formed at its outer tip with a finger piece to facilitate pivoting the toothed rack to release same from the slot in the second handle.

9. The device according to claim 6, wherein said toothed rack includes a specially-configured tooth engageable by the edge of said slot in said second handle to fix the position of the two handles to the tubular positions of said plurality of sections, said handles being releasable to another position when the toothed rack is pivoted to disengage said specially-configured tooth from the edge of the slot in the second handle.

10. An endoscope device particularly useful as an anoscope, characterized in that it includes a plurality of sections each of the configuration of a segment of a cylinder, said plurality of sections comprising a first section, a second section pivotable to said first section along one edge thereof, and a third section attachable to said first and second sections along their opposite edges to define therewith a tubular endoscope insertable into a body cavity for examining same, said third section being detachable from said first and second sections permitting said first and second sections to be pivoted to an open position wherein they define a retractor for retracting tissue in the body cavity to facilitate performing a clinical treatment therein, and a mandrel receivable within said plurality of sections of the endoscope when their tubular positions to facilitate the insertion of the endoscope into the body cavity.

11. The device according to claim 10, wherein the outer surfaces of said plurality of sections are each tapered at one end so that they together define, when in their tubular positions, a cylinder whose outer surface is conically shaped at its leading end.

12. The device according to claim 11, wherein said third section is slidably attachable to said first and second sections, said third section being formed at each of its opposite edges with a rib slidably received in a groove formed in the edge of each of said first and second sections.

13. The device according to claim 11, wherein said pivotable sections are each attaced to a handle to facilitate holding the device and pivoting said sections to their tubular or open portions, one of said handles carrying a toothed rack received within a slot formed in the other handle for releasably retaining the two handles in the tubular or open positions of the plurality of sections.

14. The device according to claim 13, wherein said toothed rack includes a specially-configured tooth engageable by the edge of said slot in said second handle to fix the position of the two handles to the tubular positions of said plurality of sections, said handles being releasable to another postion when the toothed rack is pivoted to disengage said specially-configured tooth from the edge of the slot in the second handle.

15. An endoscope device particularly useful as an anoscope, characterized in that it includes a plurality of sections each of the configuration of a segment of a cylinder, at least two of said sections being pivotable to each other to a tubular position wherein the plurality of sections define a tubular endoscope insertable into a body cavity for examining same, or to an open position wherein the pivotable sections define a retractor for retracting tissue in the body cavity to facilitate performing a clinical treatment therein; said plurality of sections comprising a first section, a second section pivotable to said first section along one edge thereof, and a third section slidably attachable to said first and second sections along their opposite edges to define therewith said tubular endoscope in said tubular portion thereof, but detachable from said first and second sections to permit them to be pivoted to their tubular portions to define said retractor.

16. The device accordig to claim 15, further including a mandrel receivable within said plurality of sections of the endoscope when in their tubular positions to facilitate the insertion of the endoscope into the body cavity.

17. The device according to claim 15, wherein said pivotable sections are each attached to a handle to facilitate holding the device and pivoting said sections to their tubular or open portions, one of said handles carrying a toothed rack received within a slot formed in the other handle for releasably retaining the two handles in the tubular or open positons of the plurality of sections.

18. The device according to claim 17, wherein said toothed rack includes a specially-configured tooth engageable by the edge of said slot in said second handle to fix the position of the two handles to the tubular positions of said plurality of sections, said handles being releasable to another position when the toothed rack is pivoted to disengage said specially-configured tooth from the edge of the slot in the second handle.

* * * * *